United States Patent [19]

Obata et al.

[11] Patent Number: 5,786,192

[45] Date of Patent: Jul. 28, 1998

[54] FARNESYL PYROPHOSPHATE SYNTHETASE AND DNA SEQUENCE ENCODING THE SAME

[75] Inventors: Shusei Obata, Nagoya; Ayumi Takeshita, Toyota; Kyozo Ogura; Tanetoshi Koyama, both of Sendai, all of Japan

[73] Assignee: Toyota Jidosha Kabushiki Kaisha, Toyota, Japan

[21] Appl. No.: 333,321

[22] Filed: Nov. 2, 1994

Related U.S. Application Data

[63] Continuation of Ser. No. 953,424, Sep. 29, 1992, abandoned.

[30] Foreign Application Priority Data

Oct. 1, 1991 [JP] Japan ................... 3-253788

[51] Int. Cl.$^6$ ................... C12N 9/10; C12N 15/54
[52] U.S. Cl. ................... 435/193; 435/320.1; 435/252.3; 435/252.33; 536/23.2
[58] Field of Search ................... 435/193, 320.1, 435/252.33, 252.3; 536/23.2

[56] References Cited

U.S. PATENT DOCUMENTS

| | | | |
|---|---|---|---|
| 4,331,762 | 5/1982 | Nakajima | 435/190 |
| 4,385,120 | 5/1983 | Atkinson | 435/194 |
| 5,082,785 | 1/1992 | Manning | 435/252.32 |

OTHER PUBLICATIONS

Fujisaki et al (1990) J. Biochem 108, 995–1000.
Wikin et al (1990) J. Biol Chem 265, 4607–4614.
Lathe (1985) J. Mol. Biol 183, 1–12.
Jaye et al (1983) Nuc. Acids Res. 11, 2325–2335.
Ullrich et al (1984) EMBO J. 3, 361–364.
Molecular and Cellular Biology, Sep. 1987, pp. 3138–3146, vol. 7(9).
The Journal of Biological Chemistry, vol. 264, No. 32, pp. 19176–19184 (1989).
Chemical Abstracts, vol. 95, 1981, 2424b.
Sagami et al., Biochem. Biophys. Res. Commun., 85:2, 572–578, Nov. 29 1978.
Takahashi et al., J. Biochem., 89:5, 1581–1587, 1981.
Fujisaki et al., J. Biochem., 99:5, 1327–1337, 1986.
Takahashi et al., J. Biochem., 92:5, 1527–1537, 1982.
Sagami et al., J. Biochem., 89:5, 1573–1580, 1981.
Fujii et al., J. Biol. Chem., 257:24, 14610–14612, 1982.
Takahashi et al., J. Biol. Chem., 255:10, 4539–4543, May 25 1980.
Sagami et al., Biochemistry, 16:21, 4616–4622, 1977.
Ishii et al., Biochem. Biophys. Res. Commun., 116:2, 500–506, Oct. 31 1983.
Ishii et al., Biochem. J., 233, 773–777, 1986.
Keenan et al., Arch. Biochem. Biophy., 161, 375–383, 1974.
Sagami et al., Biochem. Biophys. Acta, 1002, 218–224, 1989.
Yoshida et al., Biochem. Biophys. Res. Commun., 160:2, 448–452, Apr. 28 1989.
Yoshida et al., Biochem. Biophy. Acta., 995, 138–143, 1989.
Ohnuma et al., J. Biol. Chem., 266:35, 23706–23713, Dec. 15 1991.
Allen, Jr., et al., Biochemistry, 16:13, 2908–2915, 1977.
Carattoli et al., J. Biol. Chem., 266:9, 5854–5859, Mar. 25 1991.
Armstrong et al., Proc. Natl. Acad. Sci. USA, 87, 9975–9979, Dec. 1990.
Math et al., Proc. Natl. Acad. Sci. USA, 89, 6761–6764, Aug. 1992.
Misawa et al., J. Bacteriol., 172:12, 6704–6712, Dec. 1990.
Ashby et al., J. Biol. Chem., 265:22, 13157–13164, Aug. 5, 1990.
Nelson et al., Method in Enzymol., 68, 41–50, 1979.
Fujii et al., FEBS Lett, 161:2, 257–260, Sep. 1983.

*Primary Examiner*—Keith D. Hendricks
*Attorney, Agent, or Firm*—Kenyon & Kenyon

[57] ABSTRACT

A DNA sequence that encodes a stable farnesyl pyrophosphate synthetase and the use thereof are provided. DNA sequence that encodes a farnesyl pyrophosphate synthetase originating from *Bacillus stearothermophilus* is provided. By selecting *Bacillus stearothermophilus* as the gene origin of the synthetase, a production system for the synthetase, a production system for the synthetase particularly having thermal stability, can be constructed.

12 Claims, 2 Drawing Sheets

FARNESYL PYROPHOSPHATE SYNTHETASE AND DNA SEQUENCE ENCODING THE SAME

This application is a continuation of application Ser. No. 07/953,424, filed 29 Sep. 1992, now abandoned.

BACKGROUND OF THE INVENTION

1. Field of the Invention

The present invention relates to a bacterial farnesyl pyrophosphate synthetase. More specifically, the invention relates to a DNA sequence encoding a farnesyl pyrophosphate synthetase active substance originating from *Bacillus stearothermophilus*, a transformant carrying such a DNA sequence and a process for producing a farnesyl pyrophosphate synthetase active substance and farnesyl diphosphate. In accordance with the invention, accordingly, it is capable of producing the farnesyl pyrophosphate synthetase with high efficiency by the transformant.

2. Description of Related Art

Farnesyl pyrophosphate (hereinafter sometimes abbreviated as "FPP") is an important intermediate for biosynthesizing carotenoids, cholesterols, isoprenoids such as gum, and the like, and has been known to be formed by the condensation of isopentenyl pyrophosphate with 3,3-dimethylallyl diphosphate and it has also been known that its synthetase exist in many living organisms. Accordingly, it is assumed to be useful when the gene of the FPP synthetase is introduced in an appropriate host, and an isoprenoid is expected to be produced on a larger scale.

Base on the above attempts have been to study genes encoding a microorganism originated FPP synthetase and manipulations thereof and to produce the synthetase, but only enzymes originating from *Escherichia coli* have been known (*J. Biochem*. 108, page 995–100 (1990)). Moreover, the FPP synthetase originating from *Escherichia coli* is considerably unstable, and its activity is rapidly inactivated, for example, at 50° C. Furthermore, the synthetase coding genes originating from *Escherichia coli* are only introduced in another *Escherichia coli*, and no example of an attempt to introduce the same into any other microorganism has yet been described in any known literature.

SUMMARY OF THE INVENTION

In utilizing the FPP synthetase for practically producing FPP, it is insufficient to use the synthetase originating from *Escherichia coli* as described above and, therefore, the need for providing an FPP synthetase, in particular, one having thermal stability, would still exist. Accordingly, the object of the present invention is to provide a DNA sequence encoding a thermalstable FPP synthetase and to construct a thermalstable FPP production system using such a DNA sequence.

When the present inventors researched farnesyl pyrophosphate synthetase of a wide variety of microorganisms in order to solve the above problem, it has been found that *Bacillus stearothermophilus*, which has been generally known to grow at a high temperature and to produce various thermally stable enzymes as a rule, also produces an FPP synthetase and has further succeeded in expressing a corresponding gene by a genetically engineered technique, thereby achieving this invention.

Consequently, the above problem can be solved by a DNA sequence that encodes a farnesyl pyrophosphate synthetase originating from *Bacillus stearothermophilus*, a recombinant vector carrying the DNA sequence, and a recombinant microorganism cell having a gene transferred therein by the recombinant vector.

According to the present invention, there is also provided a process for producing a farnesyl pyrophosphate synthetase active substance that comprises culturing the microorganisms in a nutrient medium to produce and accumulate the synthetase active substance in the cultures, and isolating the synthetase therefrom.

According to the present invention, there is also provided use of the farnesyl pyrophosphate synthetase, i.e., a process for producing a farnesyl pyrophosphate that comprises condensating a 3,3-dimethylallyl pyrophosphate or geranyl pyrophosphate with isopentenyl pyrophosphate in the presence of a farnesyl pyrophosphate synthetase active substance to form the farnesyl pyrophosphate.

Thus, wide use of a farnesyl pyrophosphate synthetase active substance useful for producing a farnesyl pyrophosphate is possible.

BRIEF DESCRIPTION OF DRAWINGS

The present invention will be illustrated by referring to the drawings attached to the specification.

DETAIL DESCRIPTION

Figure 1:
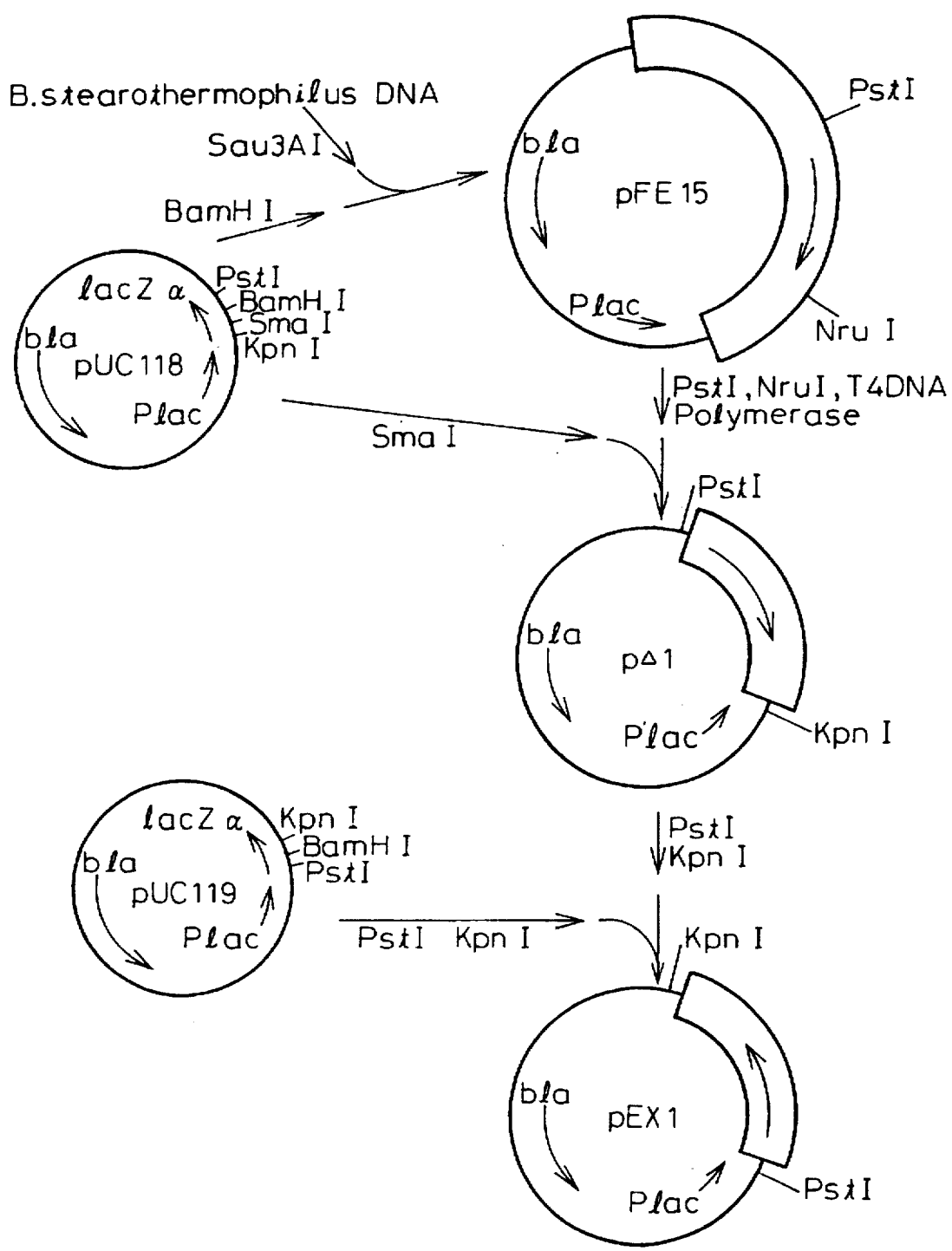
FIG. 1 is a flow chart of the construction of a recombinant plasmid according to the invention.

The term "DNA sequence which encodes a farnesyl pyrophosphate synthetase" is herein intended to mean all enzymes coding DNA units, that can express the gene encoding the synthetase, when they are incorporated into an appropriate expression vector, and is used in the conception of encompassing all enzymes encoding substantially equal enzyme active substances. Examples of them, specifically, include all DNA sequences encoding the amino acid sequences depicted on Sequence No. 1 of the Sequence Listing. Also included herein are enzymes that encode such DNA sequences and, at the same time, encode additional amino acids as long as the proteins produced by the expression have the above mentioned activity (for example, fused-proteins). Specific examples of such DNA sequences are DNA sequences as depicted on Sequence No. 1 (SEQ ID NO:1) of the Sequence Listing.

The DNA sequence of the present invention may be prepared from a chromosome of *Bacillus stearothermophilus*, which is available from various Institutes for the Deposit of Microorganisms, by any method known per se, the details of which are described later.

The invention also provides recombinant vector comprising the above-mentioned DNA sequence. Such a recombinant vector also contains a DNA sequence, and has a function of regulating the expression of gene encoding the FPP synthetase.

For example, in the case of using *Escherichia coli* in the host, it has been known that there are functions for regulating the expression of genes, such as the stage of transcription from DNA to MRNA and the stage for translation from MRNA to a protein. In addition to naturally occurring sequences, e.g., lac, trp, bla, lpp, $P_L$, $P_R$, tet, T3, T7, etc, mutants thereof, e.g., lac UV5, and sequences in which naturally occurring promoter coding sequences are artificially fused, e.g., tac, trc, etc., have been known as the promoter sequences for regulating the synthesis of mRNA.

and they can be used in the invention. In the sequences which regulate the capability of translation of a protein from mRNA, the distance between the ribosome binding site sequence (GAGG and similar sequences) and the initiation codon "ATG" has already been known to be important. It is also well known that a vector containing a terminator that directs termination of the transcription to 3'-end, e.g., a vector containing rrnBT$_1$T$_2$, which is available from Phramacia, affects the efficiency of synthesizing a protein in a recombinant.

In the DNA disclosed by this invention, the gene of FPP synthetase starts from GTG encoding rare initiation codon, but it can easily be deduced that the synthesis efficiency would be increased if it starts from ATG, which is a usual initiation codon for synthesizing a protein.

For vectors that can be used for preparing the recombinant vector of the invention, a commercially available vector itself may be useful and various vectors that are also derived according to the object may be useful. For example, such vectors include pBR322 pBR327, pKK223-3, pKK233-2, pTrc991, and the like, which possess a replicon originating from pMB1; pUC18, pUC19, pUC118, pUC119, pHSG298, pHSG396, and the like, which have been modified so as to increase the copy number; pACYC117, pACYC118, and the like, which possess a replicon originating from p15A; and plasmids derived from pSC101, ColE1 or R1, and one derived from F factor, and the like. Alternatively, other than the plasmid, it is also possible to incorporate a gene into a host cell by means of a virus vector or a transposon such as λ pharge or M13 pharge.

For the gene incorporated into microorganisms other than *Escherichia coli*, there is a gene incorporated into the microorganisms belonging to the genus Bacillus by means of pUB110 (sold by Sigma) or pHY300PLK (sold by Takara Shuzo Co., Ltd.). For these vectors, there are descriptions in Molecular cloning (J. Sambrook, E. F. Fritsch, and T. Maniatis Ed., pressed by Cold Spring Harbor Laboratory Press) and Cloning Vector (P. H. Pouwels, B. E. Enger-Valk and W. J. Brammar Ed., pressed by Elsevier), and catalogues of the producers. Particularly, pTrc 99A (sold by Pharmacia), which not only has a resistant gene to ampicillin, which is a selected marker, but also has Ptrc and lacI$^q$ as a promoter and a regulation gene, respectively, the sequence of "AGGA", as the ribosome-binding site, and rrnBT$_1$T$_2$, as the terminator, and functions to regulate the expression of an FPP synthetase, can be mentioned as a preferable vector.

The insertion of the DNA fragment that encodes an FPP synthetase and, if necessary, a DNA fragment possessing the function of regulating the expression of an FPP synthetase into these vectors can be carried out by a known method using appropriate restriction enzymes and ligase. More specifically, this is preferably conducted according to the method described below. An example of the plasmid produced as described above is pEX1. This plasmid can be obtained from *Escherichia coli* JM109 (pEX1), which has been internationally, under the Budapest Treaty, deposited at the Fermentation Reserach Institute, Agency of Industrial Science and Technology, as FERM BP-3581, on Sep. 26, 1991, by the method known per se.

As the microorganisms that can be gene-incorporated, microorganisms belonging to *Escherichia coli*, Bacillus, and the like, can be utilized. The transformation or transduction thereof may also be conducted by a conventional method such as a CaCl$_2$ method or protoplast method described, for example, in Molecular cloning (J. Sambrook, E. F. Fritsch, and T. Maniatis Ed, pressed by Cold Spring Harbor Laboratory Press), DNA Cloning Vol. I–III (D. M. Glover ed., pressed by IRL PRESS), and the like. As a representative transformat thus obtained, the above-mentioned JM109 (pEX1) (also described as pEX 1/JM109) can be considered.

When being cultured in a nutrient medium usually used in the culture of *Escherichia coli*, these transformants or recombinant accumulate farnesyl pyrophosphate in their bacterial cells, in the case of using *Escherichia coli* as the host. For example, as the nutrient medium, any of the synthesized media and natural media containing carbon sources, nitrogen sources, and mineral substances known Per se may be used. As carbon sources, carbohydrates, such as glycerol glucose, glycerine, fructose, sucrose, maltose, starches, starch hydrolyzed liquid syrups, or the like can be used. The amount used is preferably about 0.1 to 5.0%.

As nitrogen sources, various inorganic and organic ammonium salts, such as ammonia, ammonium chloride, ammonium phosphate, ammonium sulfate, and naturally originating nitrogen sources, such as amino acids, meat extracts, yeast extracts, corn steep liquors, casein hydrolyzed products, defatted soybean powder and digested products thereof, and the like may be used. The naturally originating nitrogen sources, in many cases, also serve as carbon sources, in addition to the nitrogen sources.

As the mineral substances, potassium dihydrogenphosphate, dipotassium hydrogenphosphate, magnesium sulfate, sodium chloride, copper sulfate, ferrous sulfate, manganese chloride, cobalt chloride, ammonium molybdate, boric acid, and the like can be used.

The culture is preferably carried out under aerobic conditions, such as by shaking culture or aeration culture. The culture temperature is suitably 25°–37° C., and the pH level during the culture is preferably maintained around the neutral pH level. Usually, the period of the culture is approximately 24–72 hours.

The collection of FPP from the bacterial cells can be performed by treating the bacterial cells either physically or in an environment with the presence of an appropriate lytic enzyme to be subjected to lysis, and then removing cell debris followed by general methods for the isolation and purification of an enzyme. As the lytic enzyme, the use of lysozyme is preferable, and as the physical treatment, the use of sonication is preferable. By a thermal treatment at approximately 55° C., many proteins originating from *Escherichia coli* can be removed out as insoluble precipitates. The isolation and purification of the enzyme may be carried out using various kinds of chromatography such as gel permeation, ion-exchanging, hydrophobic, reverse phase, and affinity chromatography or using superfiltration singly or in combination. As a stabilizer for stabilizing the desired enzyme throughout the isolation and purification stages, for example, reducing agents such as β-mercaptoethanol and dithiothreitol, agents for protecting protease such as PMS and BSA, metal ions such as magnesium may coexist in the liquid to be treated.

Since the activity of the above-mentioned FPP synthetase can be measured, for example, as follows, the isolation and purification are recommended to be carried out while monitoring the enzyme activity using a reaction liquid for assay described later in Example 1 c).

Furthermore, the assay system, as such or in a modified condition, can be utilized for producing the farnesyl pyrophosphate via condensation of geranyl pyrophosphate with isopentenyl pyrophosphate in the presence of the FPP synthetase.

[Working Examples]

Examples of the preparation of the DNA sequence, plasmid, and transformant according to this invention will be described below, but the scope of this invention should not be restricted thereto.

Example 1

The experiment was carried out mainly following the procedures described in the above mentioned "Molecular cloning", "DNA Cloning" and "catalogue of Takara Shuzo Co., Ltd.". Enzymes used were mainly purchased from Takara Shuzo Co., Ltd.. *Bacillus stearothermophilus* used in a known bacterium deposited at American Type Culture Collection (ATCC). In this study, ATCC 10149 strain was used.

a) Preparation of Chromosomal DNA of *Bacillus stearothermophilus*

The strain was cultured in an LB medium (1% Trypton, 0.5% Yeast extract, 1% NaCl) and the cells were collected. After being suspended the cells in a lysis buffer, as described below, an amount of lysozyme (produced by Sigma, originating from avian albumen) was added so as to attain 10 mg/ml suspension. After lysis, 1/10 the amount of 1M Tris; HCl(pH 8.0), 1/10 the amount of 10% SDS, 1/50 the amount of 5M NaCl were added. Proteinase K (produced by Sigma) was added so as to attain 10 mg/ml mixture, and the mixture was heated to 50° C.

An equivalent amount of phenol was added, and the mixture was gently stirred, after which centrifugation was carried out to remove proteins. The centrifuged supernatant was transferred to a beaker by means of a wide mouthed pipet. After 2.5 times the amount of ethanol were overlaid, a chromosomal DNA was wounded by means of a glass rod. After being dissolved in a TE solution (10 mM Tris·HCl, pH 8.0, 1 mM EDTA), the solution was treated with RNase A (produced by Sigma), with Proteinase K, and with phenol, after which ethanol was gently overlaid, and the chromosomal DNA was wound by means of a glass rod. After being washed with 70% ethanol, the chromosomal DNA was dissolved in the TE solution to be ready for the following experiment.

b) Preparation of Gene Library of *Bacillus stearothermophilus*

The chromosomal DNA was subjected to a partially digestion with restriction enzyme Sau3AI, and then to electrophoresis. An agarose containing DNA fragments from 2 kb.p. to 5 kb.p. was fractionated, and the DNA was extracted therefrom. The DNA was inserted into a BamHI restriction site on plasmid pUC118 (purchased from Takara Shuzo Co. Ltd.) using T4 DNA ligase to transform *Escherichia coli* JM109 strain. The library prepared as described above was used for screening.

c) Screening of Gene Encoding Isoprenoid Synthetase from the Library

The transformant from the library was cultured overnight in 30 ml of an LB medium containing 50 ug/ml of ampicillin, and the cells were collected. They were suspended in 3 ml of a sonic buffer, as described below, and the cells were lysed by sonication. The lysate were heated to 50° C. for 1 hour to inactivate the prenyltransferase originating from *Escherichia coli*, modified proteins originating *Escherichia coli* were centrifugally removed, and 600 μl of sample were used for the assay. The solution for the assay was reacted for 1 hour or 2 hour at 55° C. The reacted solution was extracted with 1-butanol, and the radioactivity was determined by a liquid scintillation counter.

In the screening as described above, strong prenyltransferase was observed in pFE15.

Subsequently, the 1-butanol extract of JM109 having pFE15 which had been reacted as described above was analyzed by thin layer chromatography (TLC). As a result, the thus formed isoprenoid was identified as farnesyl pyrophosphate, and pFE15 was confirmed to contain a gene encoding a farnesyl pyrophosphate synthetase.

While the original *Escherichia coli* did not have any prenyltransferase having an activity at 55° C., the *Escherichia coli* transformed with pFE15 had a prenyltransferase activity at 55° C. The pFE15-coded prenyltransferase originating from *Bacillus stearothermophilus* was shown here to be very stable. The results are shown in Table 1. Here, the recombinant was shown to be effective for producing a stable farnesyl pyrophosphate.

Figure 2:
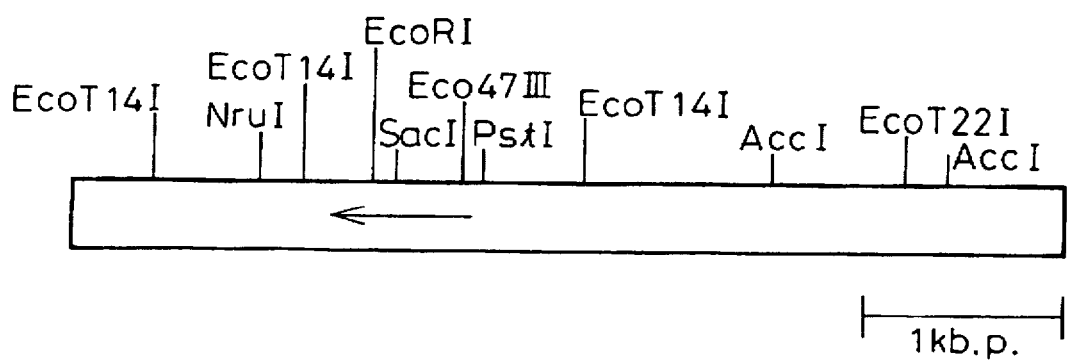
FIG. 2 is a restriction enzymes map of the plasmid pFE 15 according to the invention.

| The results of Determination of Prenyltransferase Activity (Radio-Activity of 1-Butanol Extract represented as dpm unit) | | |
|---|---|---|
| JM109 | pUC118/JM109 | pFE15/JM109 |
| $6.3 \times 10^2$ | $7.8 \times 10^2$ | $1.2 \times 10^5$ | d) Production of pFE15-Deletion Mutant and Specification of FPP-Synthesizing Enzyme pFE15 has an inserted gene of about 5 kb.p. and the restriction enzyme map is shown in FIG. 2. Of pFE15-deletion mutants, all the mutants containing the region from PstI to NruI were confirmed to possess an prenyltransferase activity. The plasmid pΔ1 in which about 2 kb.p. DNA fragment of PstI-NruI of pFE15 had been inserted in the SmaI site of pUC118 was observed to possess FPP synthetase activity. Whereas the activity remained when the portion of NruI of pΔ1 was deleted about 600 b.p., no activity remained when the PstI side was deleted about 100 b.p. Consequently, the gene encoding FPP synthetase was deduced to be at the PstI side slightly apart from NruI.

e) DNA sequencing of pΔ1

The DNA sequence of the deletion mutant produced with Exonuclease III or restriction enzymes was analyzed by an Applied Biosystem Model 373A florescent DNA sequencer. As a result, it was clarified to possess the base sequence depicted on Sequence No. 1 of the Sequence Listing and further it was deduced to possess an amino acid sequence appearing at the same time. When the deduced amino acid sequence was compared with the farnesyl pyrophosphate synthetase originating from *Escherichia coli* (*J. Biochem.* 108, page 995–100 (1990)), there was about 40% homology, confirmed to be a farnesyl pyrophosphate synthetase.

f) Production of Prenyltransferase Using lac Promoter

The plasmid pEX1 in which KpnI-pstI fragment of pΔ1 had been inserted in KpnI-PstI site of pUC119 was prepared (FIG. 1). Whereas in the pΔ1, the lac promoter and FPP synthetase gene have reversed direction to each other, in the pEX1, the lac promoter and FPP synthetase gene have the same direction. Subsequently, *Escherichia coli* JM109 was transformed with pEX1 and pΔ1, and the prenyltransferase activities were determined by the method described in section c). As a result, it was found that pEX1/JM109 had a prenyltransferase activity 15 times that of pΔ1/JM109, resulting in the productivity of FPP synthetase having been successfully improved with lac-promoter.

| (Buffer: Lysis buffer) | |
|---|---|
| Sucrose | 3 M |
| Tris.HCl (pH 8.0) | 25 mM |
| EDTA | 10 mM |
| (Buffer: Sonication buffer | |
| Tris.HCl (pH 8.5) | 50 mM |
| EDTA | 1 mM |
| β-Mercaptoethanol | 10 mM |
| PMSF | 1 μg/ml |
| Phospholamidon | 1 μg/ml |

| (Composition of reaction solution for assay (total 1 ml) | |
|---|---|
| [1-$^{14}$C] isopentenyl pyrophosphate (produced by Amersham, corresponding to about $5.5 \times 10^5$ dpm) | 25 nmol |
| Geranyl pyrophosphate | 5 μmol |
| MgCl$_2$ | 50 μmol |
| KF | 5 μmol |
| β-Mercaptoethanol | 50 μmol |
| Tris.HCl (pH 8.5) | 50 μmol |
| Tris.HCl (pH 8.5) | 50 μmol |
| Cell-free extract | 600 μl |

We claim:

1. A composition comprising isolated nucleic acid molecules containing a *Bacillus stearothermophilus* sequence encoding Farnesyl Pyrophosphate Synthetase, wherein the amino acid sequence of said Farnesyl Pyrophosphate Synthetase consists of the amino acid sequence shown in Sequence ID NO. 1.

2. An isolated recombinant nucleic acid containing a *Bacillus stearothermophilus* sequence encoding Farnesyl Pyrophosphate Synthetase, wherein the amino acid sequence of said Farnesyl Pyrophosphate Synthetase consists of the amino acid sequence shown in Sequence ID NO. 1.

3. A composition according to claim 1, comprising a sequence selected from the group consisting of:

(a) SEQ ID NO:1; and (b) Nucleic acid sequences complementary to SEQ ID NO. 1.

4. An isolated nucleic acid containing a *Bacillus stearothermophilus* sequence encoding Farnesyl Pyrophosphatase selected from the group consisting of:

(a) SEQ ID NO:1; and (b) Nucleic acid sequences complementary to SEQ ID NO. 1.

5. A recombinant vector comprising a DNA sequence of claim 2 and a DNA sequence that has a function of regulating the expression of said DNA.

6. A microorganism cell having a gene encoding the farnesyl pyrophosphate synthetase transferred therein by the recombinant vector of claim 5.

7. The microorganism according to claim 6, whose host cell is a microorganism cell belonging to the genus *Escherichia*.

8. A process for producing a farnesyl pyrophosphate synthetase active substance that comprises culturing the microorganism according to claim 6 in a nutrient medium to produce and accumulate the synthetase active substance in the cultures, and isolate the farnesyl pyrophosphate synthetase therefrom.

9. A process for preparation of a farnesyl pyrophosphate that comprises condensating a 3,3-dimethylallyl pyrophosphate or a geranyl pyrophosphate with an isopentenyl pyrophosphate in the presence of the farnesyl pyrophosphate synthetase active substance produced according to claim 8 to form the farnesyl pyrophosphate.

10. A process for producing a farnesyl pyrophosphate synthetase active substance that comprises culturing the microorganism according to claim 7 in a nutrient medium to produce and accumulate the synthetase active substance in the cultures, and isolate the farnesyl pyrophosphate synthetase therefrom.

11. A process for preparation of a farnesyl pyrophosphate that comprises condensating a 3,3-dimethylallyl pyrophosphate or a geranyl pyrophosphate with an isopentenyl pyrophosphate in the presence of the farnesyl pyrophosphate synthetase active substance produced according to claim 10 to form the farnesyl pyrophosphate.

12. An isolated DNA sequence that encodes a Farnesyl Pyrophosphate Synthetase enzyme originating from *Bacillus stearothermophilus*.

* * * * *

UNITED STATES PATENT AND TRADEMARK OFFICE
CERTIFICATE OF CORRECTION

PATENT NO. : 5,786,192
DATED : 28 July 1998
INVENTOR(S) : Shusei OBATA et al.

It is certified that error appears in the above-identified patent and that said Letters Patent is hereby corrected as shown below:

| Column | Line | |
|---|---|---|
| 1 | 28 | Change "exist" to --exists--. |
| 1 | 32 | Change "Base" to --Based--; after "above" insert --,--. |
| 2 | 13 | Change "densating" to --dense--. |
| 2 | 30 | Change "DETAIL" to --DETAILED--. |
| 2 | 61 | Change "MRNA" to --mRNA--. |
| 2 | 62 | Change "MRNA" to --mRNA--. |
| 3 | 9 | Change "Phramacia" to --Pharmacia--. |
| 3 | 59 | Change "Reserach" to --Research--. |
| 3 | 63 | Change "Bacillus" to --*Bacillus*--. |
| 4 | 1 | Change "pressed" to --published--. |
| 4 | 3 | Change "pressed" to --published--. |

UNITED STATES PATENT AND TRADEMARK OFFICE
CERTIFICATE OF CORRECTION

PATENT NO. : 5,786,192
DATED : 28 July 1998
INVENTOR(S) : Shusei OBATA et al.

It is certified that error appears in the above-identified patent and that said Letters Patent is hereby corrected as shown below:

| Column | Line | |
|---|---|---|
| 5 | 24 | Change "HCl(pH 8.0)" to --HCl•(pH 8.0)--. |
| 5 | 33 | Change "wounded" to --wound--. |
| 5 | 45 | Change "a partially" to --partial--. |
| 7 | 7 | Change "Tris.HCl" to --Tris•HCl--. |
| 7 | 12 | Change "Tris.HCl" to --Tris•HCl--. |
| 8 | 13 | Change "Tris.HCl" to --Tris•HCl--. |
| 8 | 14 | Change "Tris.HCl" to --Tris•HCl--. |
| 10 | 47 | Change "condensating" to --condensing--. |
| 10 | 58 | Change "condensating" to --condensing--. |

Signed and Sealed this

Twelfth Day of December, 2000

Attest:

Q. TODD DICKINSON

*Attesting Officer*   *Director of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 893 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Bacillus stearothermophilus ( x i ) SEQUENCE DESCRIPTION: SEQ ID NO:1:

```
ATG GCG CAG CTT TCA GTT GAA CAG TTT CTC AAC GAG CAA AAA CAG GCG      48
Met Ala Met Leu Ser Val Glu Gln Phe Leu Asn Glu Gln Lys Gln Ala
 1               5                  10                  15

GTG GAA ACA GCG CTC TCC CGT TAT ATA GAG CGC TTA GAA GGG CCG GCG      96
Met Glu Thr Ala Leu Ser Arg Tyr Ile Glu Arg Leu Glu Gly Pro Ala
                20                  25                  30

AAG CTG AAA AAG GCG ATG GCG TAC TCA TTG GAG GCC GGC GGC AAA CGA     144
Lys Leu Lys Lys Ala Met Ala Tyr Ser Leu Glu Ala Gly Gly Lys Arg
             35                  40                  45

ATC CGT CCG TTG CTG CTT CTG TCC ACC GTT CGG GCG CTC GGC AAA GAC     192
Ile Arg Pro Leu Leu Leu Leu Ser Thr Val Arg Ala Leu Gly Lys Asp
         50                  55                  60

CCG GCG GTC GGA TTG CCC GTC GCC TGC GCG ATT GAA ATG ATC CAT ACG     240
Pro Ala Val Gly Leu Pro Val Ala Cys Ala Ile Glu Met Ile His Thr
 65                  70                  75                  80

TAC TCT TTG ATC CAT GAT GAT TTG CCG AGC ATG GAC AAC GAT GAT TTG     288
Tyr Ser Leu Ile His Asp Asp Leu Pro Ser Met Asp Asn Asp Asp Leu
                 85                  90                  95

CGG CGC GGC AAG CCG ACG AAC CAT AAA GTG TTC GGC GAG GCG ATG GCC     336
Arg Arg Gly Lys Pro Thr Asn His Lys Val Phe Gly Glu Ala Met Ala
                100                 105                 110

ATC TTG GCG GGG GAC GGG TTG TTG ACG TAC GCG TTT CAA TTG ATC ACC     384
Ile Leu Ala Gly Asp Gly Leu Leu Thr Tyr Ala Phe Gln Leu Ile Thr
            115                 120                 125

GAA ATC GAC GAT GAG CGC ATC CCT CCT TCC GTC CGG CTT CGG CTC ATC     432
```

-continued

| | | | | | | | | | | | | | | |
|---|---|---|---|---|---|---|---|---|---|---|---|---|---|---|
| Glu | Ile | Asp | Asp | Glu | Arg | Ile | Pro | Pro | Ser | Val | Arg | Leu | Arg | Leu | Ile |
| | 130 | | | | | 135 | | | | | 140 | | | | |

| GAA | CGG | CTG | GCG | AAA | GCG | GCC | GGT | CCG | GAA | GGG | ATG | GTC | GCC | GGT | CAG | 480 |
|---|---|---|---|---|---|---|---|---|---|---|---|---|---|---|---|---|
| Glu | Arg | Leu | Ala | Lys | Ala | Ala | Gly | Pro | Glu | Gly | Met | Val | Ala | Gly | Gln | |
| 145 | | | | | 150 | | | | | 155 | | | | | 160 | |

| GCA | GCC | GAT | ATG | GAA | GGA | GAG | GGG | AAA | ACG | CTG | ACG | CTT | TCG | GAG | CTC | 528 |
|---|---|---|---|---|---|---|---|---|---|---|---|---|---|---|---|---|
| Ala | Ala | Asp | Met | Glu | Gly | Glu | Gly | Lys | Thr | Leu | Thr | Leu | Ser | Glu | Leu | |
| | | | | 165 | | | | | 170 | | | | | 175 | | |

| GAA | TAC | ATT | CAT | CGG | CAT | AAA | ACC | GGG | AAA | ATG | CTG | CAA | TAC | AGC | GTG | 576 |
|---|---|---|---|---|---|---|---|---|---|---|---|---|---|---|---|---|
| Glu | Tyr | Ile | His | Arg | His | Lys | Thr | Gly | Lys | Met | Leu | Gln | Tyr | Ser | Val | |
| | | | 180 | | | | | 185 | | | | | 190 | | | |

| CAC | GCC | GGC | GCC | TTG | ATC | GGC | GGC | GCT | GAT | GCC | CGG | CAA | ACG | CGG | GAG | 624 |
|---|---|---|---|---|---|---|---|---|---|---|---|---|---|---|---|---|
| His | Ala | Gly | Ala | Leu | Ile | Gly | Gly | Ala | Asp | Ala | Arg | Gln | Thr | Arg | Glu | |
| | | 195 | | | | | 200 | | | | | 205 | | | | |

| CTT | GAC | GAA | TTC | GCC | GCC | CAT | CTA | GGC | CTT | GCC | TTT | CAA | ATT | CGC | GAT | 672 |
|---|---|---|---|---|---|---|---|---|---|---|---|---|---|---|---|---|
| Leu | Asp | Glu | Phe | Ala | Ala | His | Leu | Gly | Leu | Ala | Phe | Gln | Ile | Arg | Asp | |
| | 210 | | | | | 215 | | | | | 220 | | | | | |

| GAT | ATT | CTC | GAT | ATT | GAA | GGG | GCA | GAA | GAA | AAA | ATC | GGC | AAG | CCG | GTC | 720 |
|---|---|---|---|---|---|---|---|---|---|---|---|---|---|---|---|---|
| Asp | Ile | Leu | Asp | Ile | Glu | Gly | Ala | Glu | Glu | Lys | Ile | Gly | Lys | Pro | Val | |
| 225 | | | | | 230 | | | | | 235 | | | | | 240 | |

| GGC | AGC | GAC | CAA | AGC | AAC | AAC | AAA | GCG | ACG | TAT | CCA | GCG | TTG | CTG | TCG | 768 |
|---|---|---|---|---|---|---|---|---|---|---|---|---|---|---|---|---|
| Gly | Ser | Asp | Gln | Ser | Asn | Asn | Lys | Ala | Thr | Tyr | Pro | Ala | Leu | Leu | Ser | |
| | | | | 245 | | | | | 250 | | | | | 255 | | |

| CTT | GCC | GGC | GCG | AAG | GAA | AAG | TTG | GCG | TTC | CAT | ATC | GAG | GCG | GCG | CAG | 816 |
|---|---|---|---|---|---|---|---|---|---|---|---|---|---|---|---|---|
| Leu | Ala | Gly | Ala | Lys | Glu | Lys | Leu | Ala | Phe | His | Ile | Glu | Ala | Ala | Gln | |
| | | | 260 | | | | | 265 | | | | | 270 | | | |

| CGC | CAT | TTA | CGG | AAC | GCC | GAC | GTT | GAC | GGC | GCC | GCG | CTC | GCC | TAT | ATT | 864 |
|---|---|---|---|---|---|---|---|---|---|---|---|---|---|---|---|---|
| Arg | His | Leu | Arg | Asn | Ala | Asp | Val | Asp | Gly | Ala | Ala | Leu | Ala | Tyr | Ile | |
| | | 275 | | | | | 280 | | | | | 285 | | | | |

| TGC | GAA | CTG | GTC | GCC | GCC | CGC | GAC | CAT | TA | | | | | | | 893 |
|---|---|---|---|---|---|---|---|---|---|---|---|---|---|---|---|---|
| Cys | Glu | Leu | Val | Ala | Ala | Arg | Asp | His | | | | | | | | |
| | 290 | | | | | 295 | | | | | | | | | | |